(12) United States Patent
Donndelinger

(10) Patent No.: US 8,216,808 B2
(45) Date of Patent: Jul. 10, 2012

(54) METHODS FOR ACCELERATING TISSUE PROCESSING

(76) Inventor: Thomas M. Donndelinger, Nampa, ID (US)

( * ) Notice: Subject to any disclaimer, the term of this patent is extended or adjusted under 35 U.S.C. 154(b) by 740 days.

(21) Appl. No.: 12/316,056

(22) Filed: Dec. 9, 2008

(65) Prior Publication Data

US 2010/0144002 A1      Jun. 10, 2010

(51) Int. Cl.
*C12P 19/00* (2006.01)
(52) U.S. Cl. .... 435/72; 435/40.5; 435/40.51; 435/40.52
(58) Field of Classification Search ................ 435/40.5, 435/40.51, 40.52
See application file for complete search history.

(56) References Cited

U.S. PATENT DOCUMENTS 6,291,180 B1 * 9/2001 Chu .............................. 435/6.11
2005/0054958 A1 * 3/2005 Hoffmann ....................... 601/46

FOREIGN PATENT DOCUMENTS

JP    2008-224367        9/2008
WO   2005-019836 A2    3/2005

\* cited by examiner

*Primary Examiner* — Bao Thuy L Nguyen
(74) *Attorney, Agent, or Firm* — Kirton McConkie; Evan R. Witt

(57) ABSTRACT

Systems and methods for accelerating tissue processing by treating tissue samples and one or more tissue processing agents with infrasonic vibrations are discussed. Some non-limiting examples of tissue processing agents include a tissue fixative, dehydrating agent, clearing agent, impregnating agent, embedding agent, tissue stain, enzyme, or another chemical that diffuses into the tissue sample when the sample is being preserved or prepared for microscopic examination. The infrasonic vibrations can have a frequency from about 10 to about 600 Hz. The infrasonic vibrations can have an amplitude that is sufficiently high, when combined with the frequency, to induce turbulent mixing of the processing agent and accelerate tissue processing. The tissue sample may optionally be vibrated with ultrasonic vibrations. The ultrasonic vibrations can have a frequency and amplitude that are sufficiently high to induce turbulent mixing of the processing agent and to accelerate tissue processing.

20 Claims, 5 Drawing Sheets

(3 of 5 Drawing Sheet(s) Filed in Color)

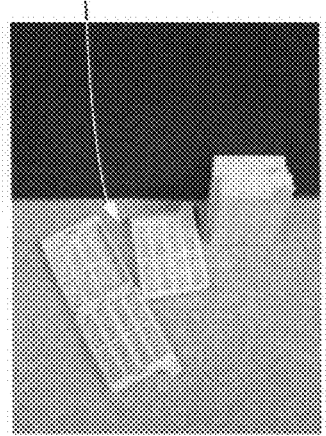
Fig. 5A – Tissue Cassettes
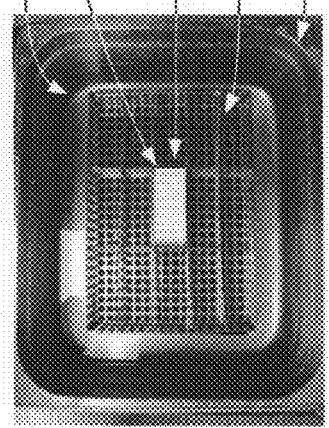
Fig. 5B – Set Up
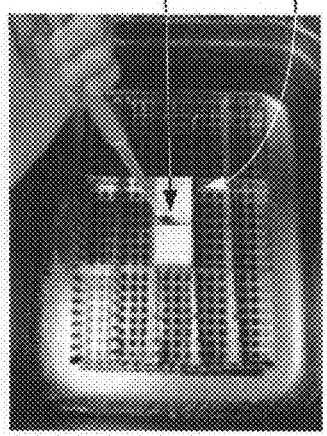
Fig. 5C – Adding Dye
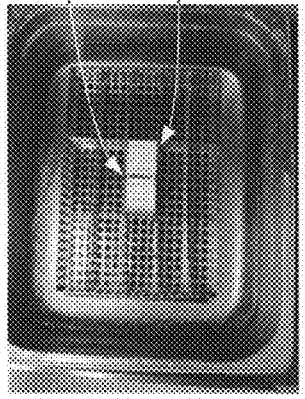
Fig. 5D – 30 Seconds
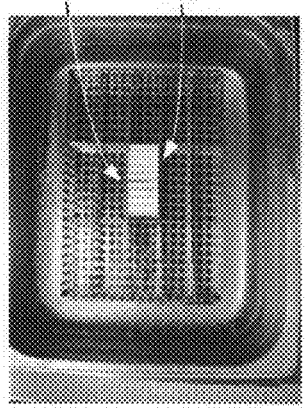
Fig. 5E – 5 Minutes
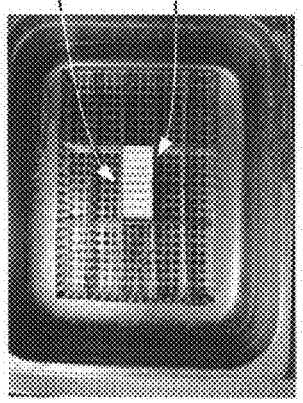
Fig. 5F – 10 Minutes
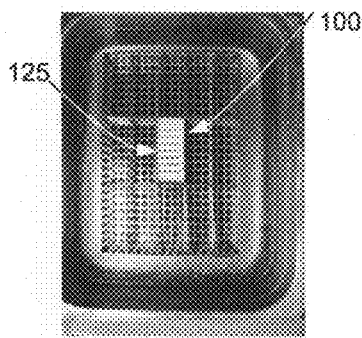
Fig. 5G – 20 Minutes

METHODS FOR ACCELERATING TISSUE PROCESSING

BACKGROUND

1. Field

This application relates generally to systems and methods for accelerating tissue processing. More specifically, this application relates to systems and methods for accelerating tissue fixation, dehydration, and/or other aspects of tissue processing through the use of infrasonic vibrations.

2. Background

Tissue samples may include one or more cells, tissues, organs, or other materials obtained from an organism, as well as the entire organism or a portion thereof. Such tissue samples may be useful in the study and practice of medicine, histology, pathology, cellular biology, and the biological sciences in general. For instance, tissue samples may be useful for the diagnosis of disease or may aid in the study of diseases, disorders, functions, structures, and other characteristics of biological specimens. Although tissue samples may be obtained in many ways, including from autopsy, biopsy, surgery, necropsy, etc., once obtained, the samples are often unable to regulate proteolytic enzymes and other processes that tend to break down and degrade biological material.

In order to preserve a sample's structure or morphology, as well as to conserve the presence and reactivity of biochemicals in the sample, tissue samples are often processed to be preserved by freezing or by chemical fixation. Where a sample is frozen, the sample is often frozen, cut, and mounted to a slide in a short period of time, such as about 15 minutes. This frozen section procedure can allow for rapid histological diagnosis to be made from a sample. As a result, this process is frequently used in situations where a diagnosis is necessary during a surgical operation. However, this frozen section procedure can also have certain disadvantages. For example, samples prepared by this procedure may not possess the same level of uniformity and quality as samples prepared by another process. Similarly, samples prepared by this frozen section procedure may need to be extra thick and require special stains that are difficult to use. Moreover, this frozen section procedure may cause other artifacts associated with freezing and may put the sample at a high risk of being damaged by thawing or refreezing. For at least the aforementioned reasons, this frozen section procedure may reduce the quality of the tissue samples and cause the processed samples to lack important detail.

Generally, fixation is a chemical process that prevents tissue sample decay by terminating ongoing biochemical reactions. This process may also increase the mechanical strength or stability of the treated samples. There are many fixation processes as well as reagents. For instance, tissue samples may be fixed with a cross-linking fixative, such as an aldehyde-based fixative, that is believed to react with proteins and other molecules in the tissue sample to form methylene bridges. The methylene bridges may produce a network of chemical bonds that can prevent the movement of large molecules, such as proteins, and substantially preserve the physical structure of the tissue sample. After fixation, destructive enzymes may be prevented from further degrading the tissue sample.

In addition to tissue fixation, tissue processing may involve several additional stages that further preserve the tissue sample or prepare it for examination. For instance, the fixed tissue sample may be dehydrated, cleared, impregnated with and embedded in a material (e.g., paraffin or gelatin), cut into sections, cleared, mounted to a slide, stained, treated with enzymes, treated with antibodies, treated for antigen retrieval, and/or otherwise be prepared for microscopic examination.

Although tissue processing methods that involve fixation may allow tissue samples to be studied long after the natural expiration of the samples would have occurred, these methods are not without shortcomings. For instance, artifacts may be produced by incomplete fixation. Additionally, some conventional tissue processing methods that involve fixation may be quite time consuming and require processing times that last from several hours to several days.

To speed conventional tissue processing methods that include fixation, some have implemented one or more additional processing steps. In one example, some have begun using ultrasonic vibrations to speed tissue processing. However, in certain circumstances, these ultrasonic vibrations can focally overheat and damage the tissue sample. In another example, some have begun heating or microwaving the tissue sample at different tissue processing steps. However, because temperatures above 37° Celsius can unfold, refold, aggregate, and/or denature proteins within the sample, such heating and microwaving steps may locally overheat and damage the tissue sample. Indeed, many conventional methods to speed tissue processing may damage tissue samples, damage cell morphology, cause DNA/RNA degradation, require antigen retrieval, cause additional artifacts, or otherwise impede proper tissue analysis.

Thus, while techniques currently exist that are used to speed tissue processing (i.e., fixation), challenges still exist, including those listed above. Accordingly, it would be an improvement in the art to augment or even replace current techniques with other techniques that speed tissue processing and, which may more thoroughly fix a tissue sample or otherwise improve the sample's detail.

BRIEF SUMMARY

The present invention relates to systems and methods for accelerating tissue processing. Generally, the described systems and methods include treating tissue samples with infrasonic vibrations at one or more stages of tissue processing. In one example, a tissue sample is treated with infrasonic vibrations while the sample is in contact with a tissue processing agent. Some non-limiting examples of tissue processing agents include one or more tissue fixatives, dehydrating agents, clearing agents, impregnation agents, embedding agents, tissue stains, antibodies, enzymes, and/or other chemicals that can be used to extend the storage time of the sample or to prepare the sample for microscopic examination.

When a tissue processing agent is not disturbed, a concentration boundary layer forms around the tissue sample. Within this boundary layer, the concentration of the processing agent varies from a maximum concentration, which is associated with the bulk processing agent, to a minimum concentration, which occurs where the processing agent diffuses into the tissue sample. Thus, in a tissue sample that is fixed with no movement of the fixative, diffusion leading to fixation requires a longer amount of time than does diffusion for a tissue sample in which the fixative agent is mixed or disturbed with infrasonic vibrations.

It is theorized that infrasonic vibrations may provide the processing agent with a true non-depleted reservoir at the boundary layer between the surface of the tissue sample and the bulk processing agent. For instance, as the infrasonic vibrations produce turbulent mixing, or a mixing that is achieved when the vibrations have an amplitude and frequency that are sufficiently high to result in a Reynolds number characteristic of turbulent mixing, the turbulent mixing transports fresh processing agent to the boundary layer adjacent to the tissue sample. As this turbulent mixing creates the true non-depleted reservoir, it may also allow for Fick's law (concerning diffusion) to be fulfilled. Accordingly, the infrasonic vibrations result in the efficient diffusion of the processing agent into the tissue sample.

The infrasonic vibrations can have any frequency that accelerates one or more stages of tissue processing (e.g., fixation and dehydration). For example, the infrasonic vibrations can have a frequency selected from about 5 to about 1,000 Hz; about 10 to about 600 Hz; about 20 to about 100 Hz; about 40 to about 80 Hz; or about 50 to about 70 Hz (e.g., about 60 Hz±5 Hz). It should be noted, however, that the desired frequency of the infrasonic vibrations may be varied from one processing agent to another, from one stage of tissue processing to another, from one vibration mechanism to another, and so forth.

Moreover, the infrasonic vibrations may have any amplitude in combination with the frequency that is sufficiently high to provide the processing agent with a Reynolds number that is characteristic of turbulent mixing while being low enough to not cause vibration damage to the tissue sample. In other words, the infrasonic vibrations may have any amplitude that, when combined with the vibrations' frequency, is sufficient to result in a Reynolds number that is sufficiently high to cause turbulent movement of the processing agent in contact with the tissue sample. To achieve this turbulent mixing, in some instances, the amplitude and the frequency may be varied independent of each other until processing agent transitions from a laminar state to a turbulent mixing state at the boundary layer adjacent the tissue sample.

In addition to being treated with infrasonic vibrations, the tissue sample and processing agent(s) may be optionally vibrated with ultrasonic vibrations at one or more stages of tissue processing. In such instances, the infrasonic vibrations and the ultrasonic vibrations may be applied to the sample separately and/or in combination. For example, the infrasonic and ultrasonic vibrations can be used during the same and/or different stages of tissue processing. Additionally, while the tissue sample can be vibrated with both infrasonic and ultrasonic vibrations at the same time during one or more stages of tissue processing, in some embodiments, it is beneficial to vibrate the tissue sample with the infrasonic and ultrasonic vibrations at different or non-overlapping time periods so as to avoid a beat note.

Where the tissue sample is vibrated with ultrasonic vibrations, the vibrations can have any frequency and amplitude that speeds one or more stages of tissue processing. For example, the ultrasonic vibrations can have any frequency and amplitude that is sufficient to result in a Reynolds number that is high enough to represent turbulent mixing of the processing agent that is in contact with the tissue sample.

While the frequency and amplitude of the infrasonic and ultrasonic vibrations (if included) may be kept substantially constant throughout tissue processing, in some embodiments, the frequency and or amplitude of the infrasonic and/or ultrasonic vibrations may be varied throughout a single stage or throughout the entire duration of the tissue processing.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The following description can be better understood in light of several Figures, in which:

FIGS. 5A-5G depict an experimental set up which was used to determine a presently preferred frequency at which the infrasonic vibrations may be applied to a tissue sample that is being fixed in 5% formalin.

Figure 1:
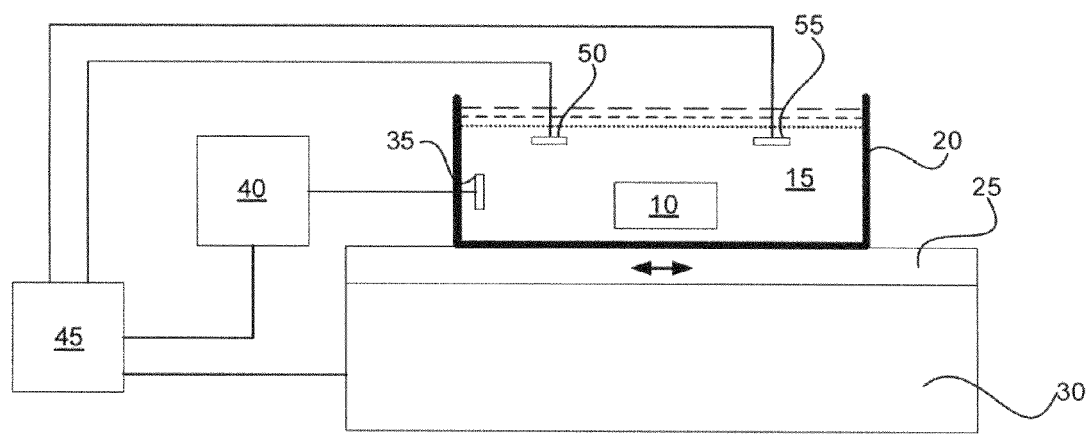
FIG. 1 illustrates a representative embodiment of a system for accelerating tissue processing with infrasonic vibrations.

Together with the following description, the Figures help demonstrate and explain the principles of the described methods and systems.

DETAILED DESCRIPTION

The presently preferred embodiments of the described invention may be understood by reference to the following description. It will be appreciated that the described systems and methods, as generally described herein, may be arranged and designed in a wide variety of manners. Thus, the following more detailed description of some embodiments of the present invention is not intended to limit the scope of the invention, as claimed, but is merely representative of presently preferred embodiments of the invention.

Under a non-binding theory, tissue samples placed in a tissue processing agent (e.g., a tissue fixative) develop a concentration boundary layer between the surface of the tissue sample and the bulk processing agent concentration. In this typical concentration boundary, the processing agent, or components thereof, are less concentrated near the sample and become more concentrated at distances moving away from the sample's surface. Accordingly, this concentration boundary can slow tissue processing by limiting diffusion of the processing agent to the tissue sample. To speed tissue processing, as disclosed herein, tissue samples are vibrated with infrasonic vibrations at one or more stages during tissue processing. These infrasonic vibrations may cause turbulent mixing of the processing agent, reduce or flatten the concentration gradient of the boundary layer, and/or otherwise act to increase the rate of diffusion of the processing agent into the tissue sample.

In the described systems and methods, infrasonic vibrations can be used in virtually any tissue processing technique. In other words, the infrasonic vibrations can be used in any known or novel process in which a tissue processing agent diffuses into a tissue sample so as to preserve the tissue sample and/or prepare it for microscopic examination. Additionally, the infrasonic vibrations can be used at any stage of a tissue processing technique in which the vibrations can act to speed tissue processing. Some non-limiting examples of typical tissue processing stages can include stages in which the tissue sample is fixed, dehydrated, clarified, impregnated, embedded, stained, treated with an antibody, treated with an enzyme, or otherwise preserved or prepared for microscopic analysis by diffusing a tissue processing agent into the tissue sample.

Although, in some embodiments, the infrasonic vibrations are only applied to the tissue sample during tissue fixation and/or dehydration, in other embodiments, the infrasonic vibrations can be applied to the sample when it is in contact with any known or novel tissue processing agent. For instance, the infrasonic vibrations may be applied to the tissue sample during all of the stages of tissue processing in which a tissue processing agent diffuses into the tissue sample. As used herein, the term tissue processing agent may refer to any chemical agent that can diffuse across tissue sample membranes and act to preserve the tissue sample from decay and/or to prepare the sample for microscopic examination.

By way of non-limiting example, the infrasonic vibrations may be applied to the tissue sample while the sample is in contact with a suitable tissue fixative, such as paraformaldehyde, gluteraldehyde, formaledehyde, formalin, or another chemical that reduces sample decay by terminating ongoing biochemical reactions. In another example, the infrasonic vibrations are applied to the tissue sample when the sample is in contact with a dehydrating agent, such as ethyl alcohol, isopropyl alcohol, or another agent that reduces the tissue sample's water content. In yet another example, the infrasonic vibrations are applied to the tissue sample when it is in contact with a clearing agent, such as xylene, wood alcohol, dioxane, gasoline, or another chemical agent capable of removing the dehydrating agent. In still another example, the infrasonic vibrations are applied to the tissue sample when the sample is in contact with an impregnating agent, such as a paraffin wax. In yet another example, the infrasonic vibrations are applied to the tissue sample when it is in contact with a staining agent, such as a tissue stain (e.g., hematoxylin, eosin, etc.), a dye, an antibody (e.g., for immunohistochemistry or immunofluoresence), or another chemical that allows portions the tissue sample to be histologically analyzed and perceived (e.g., visually, radiographically, etc.). In a final non-limiting example, the infrasonic vibrations are applied to the tissue sample while the sample is in contact with any other suitable chemical that diffuses through a tissue sample membrane to preserve the sample or prepare it for microscopic examination. Some non-limiting examples of such chemicals may include solvents (e.g., dimethyl sulfoxide and water), detergents, alcohols, buffers, polymers, enzymes (e.g., proteinases, DNases, RNases, etc.), DNase inhibitors, RNase inhibitors, nucleic acid stabilizers, etc.

The infrasonic vibrations may be applied to the tissue sample for any portion of tissue processing that allows the vibrations to accelerate or otherwise improve tissue processing. For example, the infrasonic vibrations may be applied to the sample during a single stage, during multiple stages, or, as mentioned above, during all stages of a tissue processing technique. Moreover, with respect to each stage of the tissue processing technique, the infrasonic vibrations may be applied for any portion of the stage, including the entire duration of the stage.

The infrasonic vibrations that are applied to the tissue sample can have any frequency that accelerates at least a portion of tissue processing without undesirably damaging the tissue sample. As used herein, the term infrasonic may refer to any vibration frequency that is generally below the human hearing range and which is capable of accelerating at least a portion of tissue processing. In some embodiments, for example, the infrasonic vibrations are applied to the tissue sample at a frequency from about 5 to about 1,000 Hz. In other embodiments, the infrasonic vibrations are applied to the tissue sample at about 10 to about 600 Hz. In still other embodiments, the infrasonic vibrations are applied to the tissue sample with a frequency from about 20 to about 100 Hz. In yet other embodiments, the infrasonic vibrations are applied to the sample with a frequency from about 40 to about 80 Hz. Indeed, in some embodiments, the infrasonic vibrations are applied to the tissue sample at a frequency from about 50 to about 65 Hz (e.g., about 60 Hz). The frequency required to cause the processing agent to be changed to a turbulent mixing state may vary from one processing agent to another (e.g., according to fluid viscosity, density, etc.), from one tissue sample to another (e.g., according to tissue size, weight, density, etc.), from one vibrating mechanism to another (e.g., according to the amplitude of the vibrations produced by the mechanism), and so forth.

The infrasonic vibrations can be applied to the tissue sample with any power, intensity, or amplitude that induces turbulent mixing of the processing agent to accelerate at least one stage of tissue processing without undesirably damaging the tissue sample. Said differently, the infrasonic vibrations applied to the tissue sample may have any amplitude that when combined with the vibrations' frequency is sufficient to result in a Reynolds number that is high enough to represent turbulent mixing of the processing agent(s) contacting the tissue sample, but low enough to prevent the vibrations from unduly damaging the sample. In some embodiments, to achieve turbulent mixing the frequency and amplitude may be varied independently until a processing agent has a Reynolds number that is high enough to represent turbulent mixing. In other embodiments, however, either the frequency or the amplitude remains fixed while the other is varied until turbulent mixing occurs.

The desired frequency and amplitude of the infrasonic vibrations is determined for a particular experimental set up. By way of example, a user may place a container of processing agent, and optionally a tissue sample, on an infrasonic vibrating mechanism and add a drop of dye (e.g., food coloring) to the processing agent. The user may then vary the frequency and/or amplitude of the vibrations until the user observes turbulent mixing of the dye. If, however, the user notices that the turbulence of the processing agent is so high that the agent is splashing and/or sloshing within the container, the user may reduce the frequency and/or amplitude to a point where turbulent mixing is still achieved. This process may then be repeated for each processing agent, vibrating mechanism, tissue sample, or other suitable variable.

In addition to the application of infrasonic vibrations, in some embodiments, ultrasonic vibrations are also applied to the tissue sample during tissue processing. In such embodiments, the ultrasonic vibrations may be applied to the tissue sample at any time during tissue processing that acts to accelerate or otherwise improve tissue processing. By way of example, the ultrasonic vibrations may be applied to the tissue sample during a period of time that overlaps a time period in which the infrasonic vibrations are applied to the sample. In another example, however, ultrasonic vibrations are applied to the tissue sample at a time period that does not overlap the time period in which the infrasonic vibrations are applied. Indeed, because a resonance-induced beat note may be avoided where only the infrasonic or the ultrasonic vibrations are applied to the tissue sample during a given time period, such applications may be preferred.

Where ultrasonic vibrations and infrasonic vibrations are applied to the tissue sample at different times, the ultrasonic and infrasonic vibrations may still be applied to the tissue sample during one or more of the same stages and/or during different stages of tissue processing. In one non-limiting example where infrasonic and ultrasonic vibrations are applied to the tissue sample during different processing stages, infrasonic vibrations are applied to the tissue sample during tissue fixation and dehydration, and ultrasonic vibrations are applied to the tissue sample during tissue impregnation and embedding.

Where ultrasonic vibrations are applied to the tissue sample during tissue processing, the ultrasonic vibrations may have any frequency and amplitude that accelerate or otherwise improve at least a portion of tissue processing. For instance, the ultrasonic vibrations may have any frequency and amplitude that do not induce local resonance heating of tissue damage but do result in a Reynolds number that is sufficiently high to indicate turbulent mixing in the processing agent. In some embodiments, the frequency and amplitude of the ultrasonic vibrations may be varied independent of each other until turbulent mixing of the processing agent occurs. In other embodiments, however, either the frequency or the amplitude is maintained substantially constant while the other is varied until a non-damaging level of turbulent mixing occurs.

Additionally, while the frequency and/or amplitude of the infrasonic vibrations (and ultrasonic vibrations, if included) can each remain substantially constant throughout a single stage or during multiple stages of tissue processing (e.g., all processing stages in which a processing agent diffuses into the tissue sample), in some embodiments, the frequency and/or amplitude of the infrasonic vibrations may be varied during any suitable portion of tissue processing. In such embodiments, the frequency and/or amplitude of the infrasonic vibrations may be varied in any suitable manner. For example, the frequency and/or amplitude can be varied (e.g., increased and/or decreased) during a single stage and/or from one stage to another. By way of example, it may be beneficial to vary (e.g., increase) the amplitude of the infrasonic vibrations as a stage (e.g., fixation) progresses. In another example, the frequency and/or amplitude of the infrasonic vibrations may be varied depending on the characteristics of the processing agent that is in contact with the tissue sample. Some non-limiting examples of such processing agent characteristics may include viscosity, osmolarity, permeability, etc. For instance, it may be beneficial to use higher amplitude vibrations at a stage where the processing agent has a higher viscosity.

Similarly, the frequency and/or amplitude of the infrasonic vibrations may be varied and optimized according to specific tissue sample characteristics (e.g., tissue sample size, density, tissue type, thickness, water content, etc.). In one non-limiting example, it may be beneficial to apply infrasonic vibrations to a brain tissue sample at a different (e.g., lower) frequency and amplitude than would be applied to a bone tissue sample.

The infrasonic vibrations, and optional ultrasonic vibrations, can be applied to the tissue sample for any suitable period of time. Indeed, as previously stated, the vibrations can be applied to the tissue sample for all, or a portion of, one or more tissue processing stages. Additionally, the time period in which the vibrations are applied to the tissue sample may depend on the tissue sample characteristics (e.g., size, density, tissue type, thickness, water content, etc.), processing agent characteristics (e.g., viscosity, permeability, etc.), vibration amplitude, and/or vibration frequency. In some embodiments, infrasonic vibrations in the previously stated ranges may be applied to a tissue sample during pulses that last from about 0.001 seconds to about 29 seconds (e.g., between about 0.001 and about 5 seconds). As used herein, the term pulses may include periods in which infrasonic vibrations are applied to a sample, wherein these time periods are alternated with time periods in which no infrasonic vibrations are applied to the sample.

In other embodiments, infrasonic vibrations are applied to the tissue sample and tissue processing agent (e.g., a fixative) for substantially constant period of between about ½ of a minute and about 1 or more days. However, in some preferred embodiments, tissue processing (e.g., fixation, dehydration, etc.) may be accelerated by the application of infrasonic vibrations in the stated frequency and amplitude ranges for a period of time between about 15 minutes and about 3 hours. In still other embodiments, tissue processing (e.g., tissue dehydration) may be accelerated through the application of infrasonic vibrations in the stated frequency and amplitude ranges for a period of time selected from about 30 minutes to about 1 hour.

The infrasonic vibrations, and optional ultrasonic vibrations, can be applied to the tissue sample in any suitable manner. By way of example, the infrasonic vibrations may be applied to the sample through the use of a vibrating mechanism, such as a vibrating table capable of providing infrasonic vibrations, one or more infrasonic transducers, or any other suitable vibrating apparatus. Similarly, the ultrasonic vibrations can be applied to the tissue sample through the use of any vibrating apparatus capable of providing ultrasonic vibrations, such as, but not limited to, one or more ultrasonic transducers.

The infrasonic vibrations, and optional ultrasonic vibrations, are preferably produced by a vibrating mechanism that produces infrasonic vibrations in 1 dimension (e.g., linear movement). This is in contrast to vibrating mechanisms that move in 2 dimensions (e.g., orbital movement), and 3 dimensions. For instance, the vibrating mechanism (e.g., an infrasonic vibrating table or infrasonic transducer) may produce vibrations that go back and forth in any suitable direction.

Where the infrasonic vibrations are applied to the tissue sample through the use of a vibrating table, the vibrating table may comprise any table capable of applying infrasonic vibrations to the tissue sample. Some non-limiting examples of such tables may include an infrasonic, linear-vibrating tables sold by Metso Minerals, Barnstead International, Best Incorporated, Data Physics Corporation, or VIBCO.

In embodiments where the infrasonic vibrations are applied to the tissue sample through the use of a vibrating table, the vibrations may be applied to the sample in any suitable manner. By way of non-limiting example, FIG. 1 shows a representative embodiment in which a tissue sample 10 is immersed in a tissue processing agent 15 within a container 20. In this example, the container 20 is disposed on the vibrating surface 25 of an infrasonic vibrating table 30. Accordingly, as the vibrating surface 25 vibrates back and forth in 1 dimension, the infrasonic vibrations are transferred from the container 20 to the tissue processing agent 15 and the tissue sample 10.

In embodiments, where the infrasonic and/or ultrasonic vibrations are applied to the tissue sample through the use of a transducer (e.g., an infrasonic and/or an ultrasonic transducer), the transducer may comprise any transducer suitable to apply vibrations with the previously stated frequency and amplitude ranges to the tissue sample in a manner that accelerates at least a portion of tissue processing as described herein. Some non-limiting examples of suitable transducers may include a mechanism in which a current frequency is applied to a pizo-electric crystal, a mechanism that induces electromagnetic vibrations, or a mechanism that uses compressed air to induce vibrations.

Where the vibrations are applied through the use of a transducer, the vibrations may be supplied to the sample by any suitable number of transducers (e.g., 1, 2, 3, 4, or more) with any suitable number of heads (e.g., 1, 2, 3, 4, or more).

Indeed, because it may be beneficial to vibrate the tissue sample with a broad band of frequencies from the previously stated ranges, in some embodiments it may be beneficial to use more than one transducer or transducer head and to adapt each transducer or head to produce a specific range of frequencies. Moreover, the use of multiple transducers or heads may also allow the tissue sample to be exposed to vibrations from multiple directions. In some cases, the use of multiple transducers or heads may also allow the sample to receive a substantially even distribution of infrasonic and/or optional ultrasonic vibrations throughout.

In embodiments in which the described vibrations are applied to the tissue processing agent through the use of one or more transducers and/or heads, the vibrations may be applied in any suitable manner. In one example, the tissue sample is placed in a small container containing a processing agent. In turn, the small container is placed in a larger container containing water and one or more transducers. Accordingly, in this example, vibrations within the larger container are passed to the smaller container and to the tissue sample contained therein. In another example, FIG. 1 shows that, in some embodiments, one or more transducers may be placed in the same container as the tissue sample. Specifically, FIG. 1 shows a representative embodiment in which an ultrasonic transducer 35 that extends from an ultrasonic vibrator 40 is placed within the processing agent 15 in the container 20 so as to be in proximity to the tissue sample 10. In this example, the transducer 35 may be placed any suitable distance from the tissue sample 10. By way of non-limiting example, the transducer may be placed within about 10 centimeters of the tissue sample. For instance, the transducer 35 may be placed less than about 3 centimeters away from the tissue sample.

In addition to applying the described infrasonic vibrations and/or ultrasonic vibrations to the tissue sample, the described systems and methods can be used with any other apparatus, system, method, and/or technique that accelerates or otherwise improves tissue processing. For example, the infrasonic vibrations and, if included, the ultrasonic vibrations may be applied to the tissue sample while the tissue sample is being heated, cooled, placed under pressure, placed in a vacuum, treated with microwave energy, and so forth. Furthermore, in some embodiments, a feedback sensor-central processing unit ("CPU") is used to monitor and optimize the vibrations applied to the tissue sample. Because such a feedback sensor-CPU may accurately monitor the vibrations received by the tissue sample, such a sensor and CPU can be used to alter tissue processing conditions to maximize the efficiency of the tissue processing (e.g., to further decrease tissue processing time and improve the quality of the results).

While the feedback processor-CPU may function in any manner that allows it to monitor and optimize the vibrations applied to the tissue sample, FIG. 1 shows a representative embodiment in which both the infrasonic vibrating table 30 and the ultrasonic vibrator 40 comprise or are connected to a feedback processor-CPU 45. In FIG. 1, an infrasound sensor 50 monitors the infrasonic vibrations produced by the vibrating table 30 and an ultrasound sensor 55 monitors the ultrasonic vibrations produced by the ultrasonic vibrator 40. In so doing, the sensors 50 and 55 may monitor and determine how much of the vibrations are absorbed by the tissue processing agent(s) 15 and/or the tissue sample 10. The sensors 50 and 55 may further determine tissue characteristics (e.g., tissue size, density, water content, etc.). The sensors 50 and 55 may further measure whether turbulent mixing is occurring within the container 20, of the processing agent 15. Once the data received by the sensors 50 and 55 is sent to the CPU 45, the CPU 45 may analyze the data and send parameters to the infrasonic vibrating table 30 and the ultrasonic vibrator 40, which, in turn, emit the proper frequency and amplitude of infrasonic and ultrasonic vibrations, respectively. Throughout tissue processing, the sensors 50 and 55 may detect changes to the tissue's characteristics (e.g., tissue size, thickness, density, water content, solvent content, paraffin content, etc.). As this data is sent to the CPU 45, the CPU 45 may analyze the data and adjust operation of the infrasonic vibrating table 30 and/or the ultrasonic vibrator 40.

The described systems and methods for accelerating tissue processing through the use of infrasonic vibrations may offer several benefits and advantages. For example, as previously discussed, the described methods may greatly accelerate tissue processing over many conventional methods. In another example, the described systems and methods may be less destructive to the tissue sample than may some other conventional tissue processing methods that vibrate the tissue sample. Accordingly, the described method may allow for increased antigen preservation, improved morphologic detail, reduced RNA and/or DNA degradation, sharper detail, and the like. In another example, unlike some tissue processing methods that require the tissue sample to be heated, the described methods do not require the tissue sample to be heated. Accordingly, the described methods may further reduce the harmful effects associated with certain prior art tissue processing methods. In sum, the described methods may both speed processing time as well as increase the quality of the processed tissue.

EXAMPLES

Figure 2:
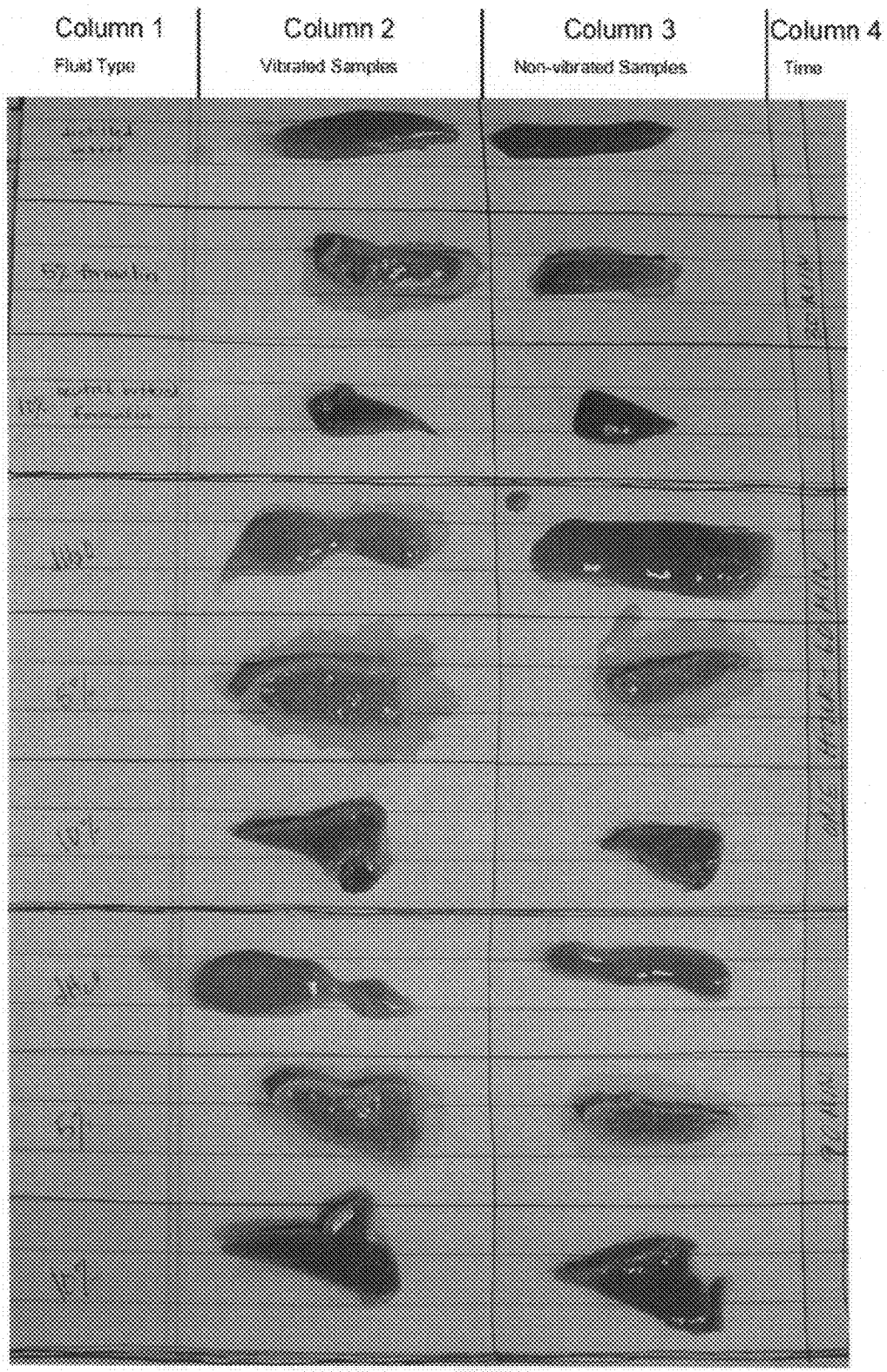
FIGS. 2 and 3 contain comparative photographs depicting experimental results of a representative method for accelerating tissue processing with infrasonic vibrations.
Figure 3:
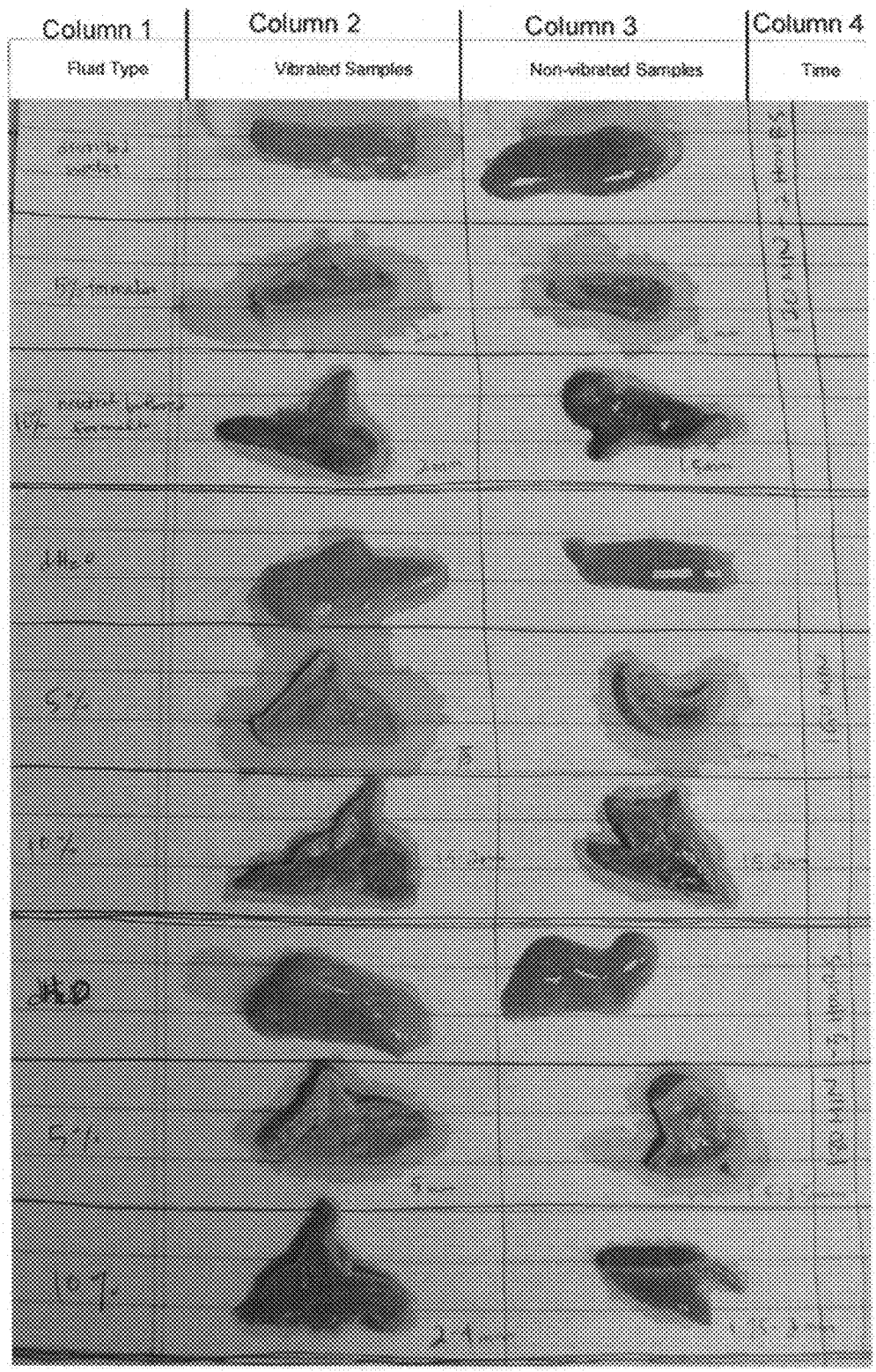
Figure 4A:
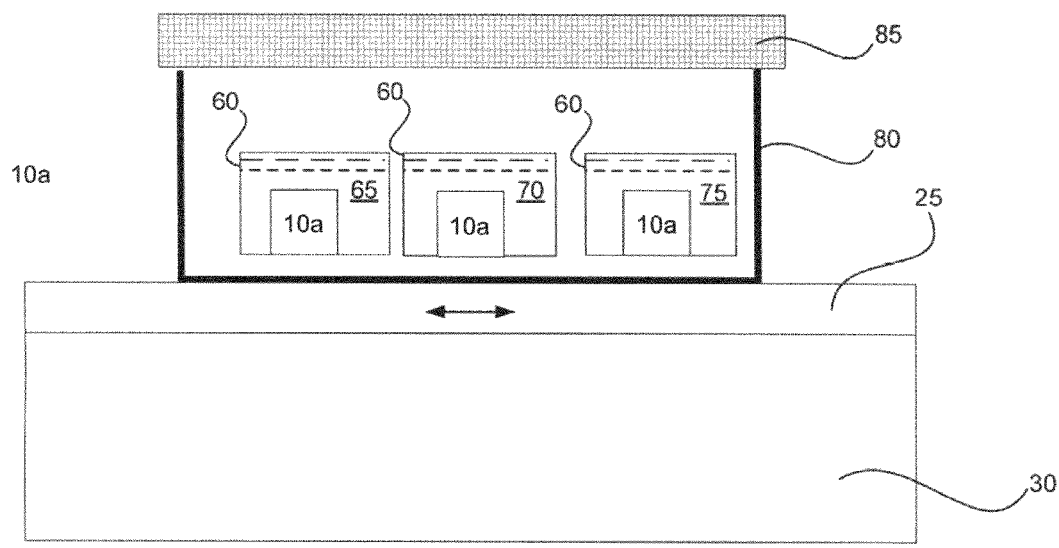
FIG. 4A depicts a representative embodiment of an experimental set up of a method for accelerating tissue processing through the use of infrasonic vibrations.
Figure 4B:
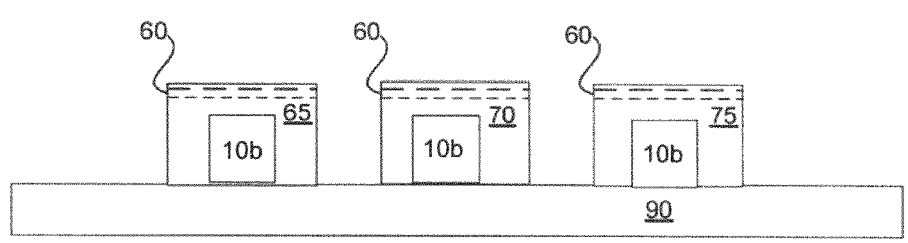
FIG. 4B depicts a representative embodiment of an experimental set up in which tissue samples and a processing agent are placed on a non-vibrating surface.

FIGS. 2 through 3 contain comparative photographs depicting experimental results from a representative method for accelerating tissue processing with infrasonic vibrations. To achieve the experimental results depicted in FIGS. 2 and 3, chicken livers were placed in distilled water, 5% formalin, and 10% neutral buffered formalin. Specifically, the experimental set up depicted in FIGS. 4A and 4B show that all of the liver samples 10a and 10b were placed in containers 60 containing fluid (e.g., distilled water 65, 5% formalin 70, or 10% neutral buffered formalin 75). Further, FIG. 4A shows that a first half of the samples 10a were placed in a box 80 on the vibrating surface 25 of the infrasonic vibrating table 30. FIG. 4A also shows that a sponge 85 was placed on top of the box 80 to dampen any sound vibrations. In contrast, FIG. 4B shows the second half of the samples 10b were placed on a non-vibrating surface (e.g., a countertop 90).

While the liver samples on the non-vibrating surface were not vibrated ("non-vibrated samples"), the samples on the infrasonic vibration table ("vibrated samples") were vibrated at an infrasonic frequency of about 60 Hz and with an amplitude sufficient to cause a Reynolds number that represents turbulent mixing. The vibrated and non-vibrated samples were left in the 3 fluids and then cut and compared at 30 minute intervals over a 3 hour time period. Once cut, the various tissue samples were photographed to illustrate the amount of fixation that occurred in each sample. The results were then recorded in the charts in FIGS. 2 and 3.

Returning to FIGS. 2 and 3, Column 1 names the type of fluid (e.g., distilled water, 5% formalin, and 10% neutral buffered formalin) that is in contact with the liver samples in Columns 2 and 3. Moreover, in FIGS. 2 and 3, Column 2 contains photographs of cross-sections of the various vibrated tissue samples that have been infrasonically vibrated for the time period indicated in Column 4. For comparison, Column 3 in FIGS. 2 and 3 contains photographs of cross-sections of the non-vibrated tissue samples that sat in the fluids with no movement for a time period indicated in Column 4. Finally, as mentioned, Column 4 identifies the approximate time period at which the samples were cut and photographed.

As observed from the liver samples in FIGS. 2 and 3, the samples placed in the distilled water act as control samples in which no fixation occurs. Accordingly, the pink coloring of all of the samples in the distilled water does not appear to change between the first cut at about 30 minutes and the last cut at about 180 minutes. In contrast, FIGS. 2 and 3 illustrate that as time in the fixatives (e.g., 5% formalin and 10% neutral buffered formalin) increases, the liver samples become increasingly fixed from the sample's outer surface towards the sample's center. More specifically, the photographs in FIGS. 2 and 3 illustrate that as the samples become fixed, the fixed portion becomes lighter and browner than the pink unfixed center portion.

A comparison between the vibrated and the non-vibrated samples in the fixatives reveals that vibrated liver samples become fixed faster than do the non-vibrated liver samples. In one example, FIG. 3 shows that in samples that were cut and photographed after being immersed in the fixatives for about 120 minutes, the vibrated samples in the 5% formalin and 10% neutral buffered formalin are each fixed to depth of approximately 2 millimeters ("mm") from the liver samples' outer surface. In contrast, FIG. 3 shows that the non-vibrated samples in the 5% formalin and the 10% neutral buffered formalin are each only fixed to a depth of about 1.5 mm. In another example, FIG. 3 shows that in samples that were cut after sitting for about 150 minutes in the fixatives, the vibrated samples in the 5% formalin and the 10% neutral buffered formalin are fixed to a depth of approximately 2.75 mm and 1.5-2 mm, respectively. In contrast, after about 150 minutes, the non-vibrated samples in the 5% formalin and the 10% neutral buffered formalin are only fixed to depth of about 2 mm and about 1.5-2 mm, respectively. In a final example, FIG. 3 shows that the vibrated samples that were cut and photographed after about 180 minutes in the fixatives are fixed to a depth of about 5 mm and about 2-4 mm, respectively. In comparison, however, after about 180 minutes, the non-vibrated liver samples that were fixed in the 5% formalin and the 10% neutral buffered formalin are fixed to a depth of about 1.5-2.5 mm and about 1.75-2 mm, respectively.

Thus, after about 180 minutes in the 5% formalin, the vibrated liver sample is fixed to a depth that is from is about 50% to about 67% deeper than is the non-vibrated liver sample, which was fixed in the 5% formalin. Similarly, after about 180 minutes in the 10% neutral buffered formalin, the vibrated sample is fixed to a depth that is up to about 56% deeper than is the corresponding non-vibrated liver sample, which was fixed with the 10% neutral buffered formalin.

FIGS. 5A through 5G illustrate an experiment which was used to determine a presently preferred frequency at which the infrasonic vibrations may be applied to a tissue sample that is being fixed in 5% formalin. Specifically, FIGS. 5A and 5B show that 9 empty tissue cassettes 100 were taken and placed in the middle well 105 of a rack 110 submersed in a dish 115 containing 5% formalin 120. The dish 115 was then placed on an infrasonic vibrating table (e.g., a METSO MINERALS® vibrating table) (not shown). Next, 50 µl of green food coloring was added to the middle cassette and the hertz dial of the table was moved between about 35 and about 70 Hz. As the dial was moved, the formalin changed from a laminar state to a turbulent mixing state at about 60 Hz. Accordingly, 60 Hz was determined to be a preferred frequency.

Following the determination of a preferred frequency, FIG. 5C shows that 50 µl of green food coloring 125 was added between the fourth and fifth cassettes 100 and the table was set to vibrate at about 60 Hz. FIGS. 5D through 5G contain pictures of the experimental set up that were taken after about 30 seconds, 5 minutes, 10 minutes, and 20 minutes of vibration, respectively. FIGS. 4D through 4G illustrate that as the vibration time progressed, the food coloring 125 propagated asymmetrically through the cassettes 100. This asymmetric propagation demonstrates that at about 60 Hz, the infrasonic vibrations may act to accelerate reagent mixing in a manner that would improve tissue processing time and thoroughness.

The present methods and systems may be embodied in other specific forms without departing from its structures, methods, or other essential characteristics as broadly described herein and claimed hereinafter. The described examples and embodiments are to be considered in all respects only as illustrative, and not restrictive. The scope of the invention is, therefore, indicated by the appended claims, rather than by the forgoing description. All changes that come within the meaning and range of equivalency of the claims are to be embraced within their scope.

The invention claimed is:

1. A method for tissue sample processing, the method comprising:
    obtaining a tissue sample;
    contacting the tissue sample with a tissue sample processing agent; and
    vibrating the tissue sample and the tissue sample processing agent with infrasonic vibrations at an amplitude and frequency that induces turbulent mixing of the processing agent to accelerate tissue processing,
    wherein the frequency of the infrasonic vibrations is from about 5 to about 1,000 Hz.

2. The method of claim 1, wherein the frequency of the infrasonic vibrations is from about 10 to about 600 Hz.

3. The method of claim 1, wherein the frequency of the infrasonic vibrations is from about 40 to about 80 Hz.

4. The method of claim 1, further comprising vibrating the tissue sample and the tissue sample processing agent with ultrasonic vibrations, wherein the ultrasonic vibrations comprise a frequency and amplitude that are sufficient to induce turbulent mixing of the processing agent to accelerate tissue processing.

5. The method of claim 4, wherein the ultrasonic vibrations are produced by an ultrasonic transducer.

6. The method of claim 4, wherein the tissue sample is vibrated with the infrasonic vibrations and the ultrasonic vibrations at non-overlapping time periods.

7. The method of claim 1, wherein the infrasonic vibrations are produced by 1 dimensional, linear vibrations.

8. The method of claim 1, wherein multiple frequencies of infrasonic vibrations are applied to the tissue sample and tissue sample processing agent.

9. The method of claim 1, wherein the tissue processing agent is selected from a tissue fixative, a dehydrating agent, a clearing agent, an impregnating agent, an embedding agent, an enzyme, an antibody, and a staining agent.

10. The method of claim 1, wherein the tissue processing agent is selected from a tissue fixative and a dehydrating agent.

11. The method of claim 1, wherein the vibrating comprises applying the infrasonic vibrations to the tissue sample and the tissue sample processing agent in pulses.

12. A method for tissue sample processing, the method comprising:
    obtaining a tissue sample;

contacting the tissue sample with a tissue processing agent selected from a tissue fixative and a dehydrating agent; and vibrating the tissue sample and the tissue processing agent with infrasonic linear vibrations at a frequency from about 10 to about 600 Hz and at an amplitude that induces turbulent mixing of the processing agent so as to accelerate tissue processing.

13. The method according to claim 12, further comprising contacting the tissue sample with a clearing agent, an impregnating agent, or a staining agent and vibrating the tissue sample with infrasonic vibrations to speed tissue processing.

14. The method of claim 12, wherein the frequency of the infrasonic vibrations is from about 55 to about 65 Hz.

15. The method of claim 12, further comprising vibrating the tissue sample and the tissue processing agent with ultrasonic vibrations at a frequency and amplitude that are sufficient to induce turbulent mixing of the processing agent.

16. The method of claim 15, wherein the tissue sample is vibrated with infrasonic and ultrasonic vibrations during different time periods.

17. The method according to claim 12, wherein the infrasonic vibrations are produced by an infrasonic vibrating table.

18. A method for tissue sample processing, the method comprising:

obtaining a tissue sample;

contacting the tissue sample with a tissue fixative; and vibrating the tissue sample and the tissue fixative with infrasonic, 1-dimensional vibrations having a frequency from about 5 to about 1,000 Hz and an amplitude that induces turbulent mixing of the tissue fixative to accelerate tissue processing, wherein the tissue sample and tissue fixative are vibrated for a time period between about 30 minutes and about 1 hour.

19. The method of claim 18, wherein the frequency of the infrasonic vibrations is from about 10 to about 600 Hz.

20. The method of claim 18, wherein the frequency of the infrasonic vibrations is about 55 to about 65 Hz.

\* \* \* \* \*